United States Patent [19]

Boettger

[11] 4,221,568

[45] Sep. 9, 1980

[54] SAMPLE PROCESSOR FOR CHEMICAL ANALYSIS

[75] Inventor: Heinz G. Boettger, La Canada, Calif.

[73] Assignee: Jet Propulsion Laboratory, Pasadena, Calif.

[21] Appl. No.: 4,044

[22] Filed: Jan. 17, 1979

[51] Int. Cl.$^2$ .......................................... G01N 31/06
[52] U.S. Cl. ............................ 23/230 R; 73/422 GC; 422/64
[58] Field of Search ...................... 73/422 GC, 423 A; 422/64, 65, 68, 69, 83, 89; 23/230 R, 230 B

[56] References Cited

U.S. PATENT DOCUMENTS

| | | | |
|---|---|---|---|
| 3,487,678 | 1/1970 | Thomson | 73/423 A |
| 3,527,101 | 9/1970 | Sprunger | 73/423 A |
| 3,536,452 | 10/1970 | Norton et al. | 422/89 |
| 3,621,719 | 11/1971 | Goodman et al. | 73/422 GC |
| 3,777,572 | 12/1973 | Hrdina | 73/423 A |
| 4,120,661 | 10/1978 | Naono | 422/68 |

*Primary Examiner*—S. Clement Swisher
*Attorney, Agent, or Firm*—Freilich, Hornbaker, Wasserman, Rosen & Fernandez

[57] ABSTRACT

An apparatus is provided which can process numerous samples that must be chemically analyzed by the application of fluids such as liquid reagents, solvents and purge gases, as well as the application of dumps for receiving the applied fluid after they pass across the sample, in a manner that permits numerous samples to be processed in a relatively short time and with minimal manpower. The processor includes a rotor which can hold numerous cartridges containing inert or adsorbent material for holding samples, and a pair of stators on opposite sides of the rotor. The stators form stations spaced along the path of the cartridges which lie in the rotor, and each station can include an aperture in one stator through which a fluid can be applied to a cartridge resting at that station, and an aperture in the other stator which can receive the fluid which has passed through the cartridge. The stators are sealed to the ends of the cartridges lying on the rotor, to thereby isolate the stations from one another.

7 Claims, 5 Drawing Figures

SAMPLE PROCESSOR FOR CHEMICAL ANALYSIS

ORIGIN OF THE INVENTION

The invention described herein was made in the performance of work under a NASA contract and is subject to the provision of Section 305 of the National Aeronautics and Space Act of 1958, Public Law 85-568 (72 Stat. 435; 42 USC 2457).

BACKGROUND OF THE INVENTION

The chemical analysis of samples is a widely encountered task, not only for the analysis of biological samples, but also those resulting from environmental monitoring and industrial process control. Where complex organic compounds must be identified and quantified, and where they may be contained in a matrix of other compounds, the analysis may be slow and costly so that it cannot be utilized in routine work. Relatively low cost assembly line processes have been developed for the analysis of a limited number of sample types, where an almost continuous supply of such samples are to be analyzed so that the equipment may be dedicated to the analysis of that particular sample type. However, such assembly line procedures utilizing largely dedicated equipment, cannot as a practical matter, be applied to a limited batch of a particular type of sample. The custom analysis of samples is prohibitive, largely because of the handling of the sample in applying reagents, solvents, and purging gases at various pressures and for controlled time periods. An apparatus that permitted the analysis of samples utilizing pressured and reactive injected fluids as well as the connection of scrubbers, gaseous waste dumps and vacuums to receive the injected fluids after passing through the sample, for controlled and often lengthy time periods, utilizing a minimal amount of operator involvement, would enable moderate cost, and therefore routine, analysis of complex samples.

SUMMARY OF THE INVENTION

In accordance with one embodiment of the present invention, a sample processor of relatively simple construction is provided, which enables the chemical analysis of a batch of samples within a limited time period and with minimal operator intervention. The processor includes a sample-holding cartridge having a pair of openings therein, and a carriage which holds the cartridge to advance it past a number of different stations. A group of fluid injectors have ports located at selected stations to inject a particular pressured fluid into a cartridge through one opening therein, and a group of fluid receivers are positioned at the same stations to receive fluid from the other port of the cartridge.

The carriage can be constructed as a rotor, with numerous cartridge-receiving through holes extending parallel to the axis of rotation of the rotor. The rotor is disposed between a pair of stators with one stator containing the fluid injector ports and the other stator containing the fluid receiving ports. Each cartridge is an elongated cylinder with openings at opposite ends, and at each station one cartridge opening is aligned with a fluid injector port while the other opening is aligned with a fluid receiving port. The rotor is advanced in an intermittent fashion, such as once every minute, to advance every cartridge thereon from one station to the next, each indexing requiring a fraction of a second. Thus, while one cartridge is receiving a reagent, another cartridge may be receiving a purging agent. Furthermore, several inactive stations may be utilized wherein there is no fluid injection, to provide the required time for the reaction of a reagent on the sample, where the reaction time may exceed the indexing time of perhaps one minute.

The cartridges can be formed of slightly greater length than the thickness of the rotor, so that they directly seal against the two stators on opposite sides of the rotor. One of the stators can be spring biased towards the other, so that the stator surfaces are pressed against the cartridge ends to form a fluid-tight seal therewith.

The novel features of the invention are set forth with particularity in the appended claims. The invention will be best understood from the following description when read in conjunction with the accompanying drawings.

DESCRIPTION OF THE PREFERRED EMBODIMENT

Figure 1:
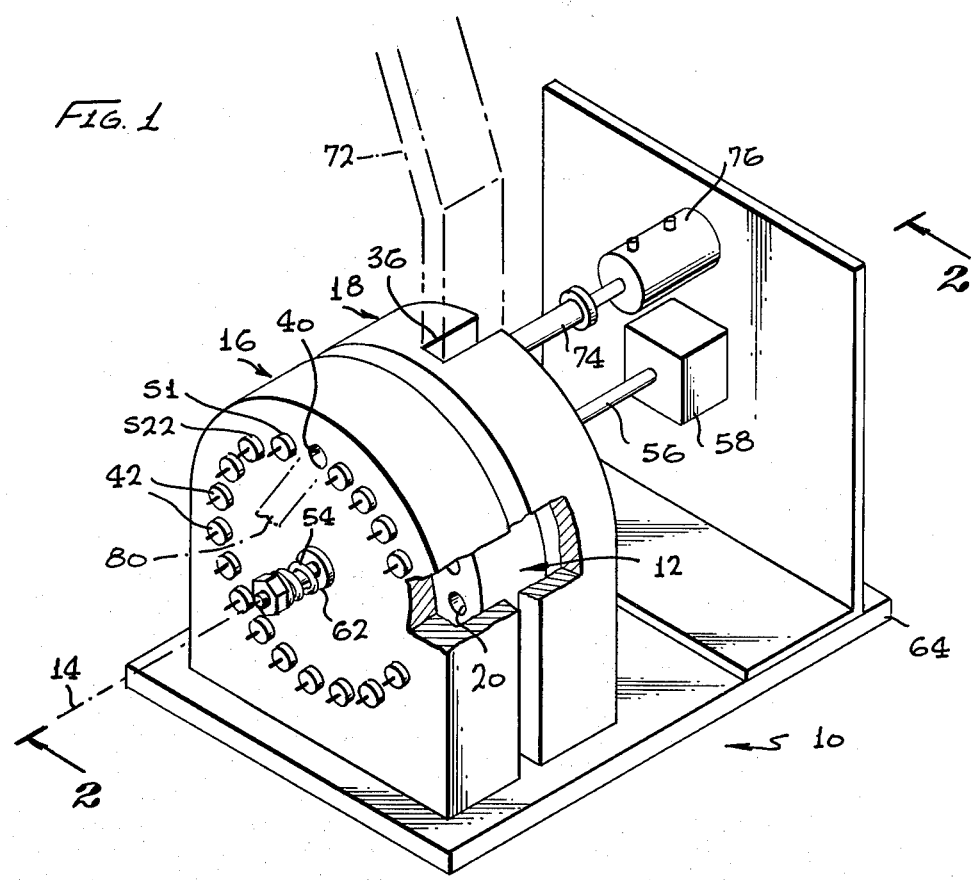
FIG. 1 is a perspective view of a sample processor constructed in accordance with the present invention.

As illustrated in FIG. 1, the sample processor 10 includes a rotor 12 which rotates about an axis 14 between a pair of stators 16, 18. The rotor has numerous through holes 20 extending parallel to the axis of rotation, for receiving a corresponding number of sample-holding cartridges. Each cartridge 22 (FIG. 3) includes a housing 24 containing an inert or adsorbant packing material 26 which can hold a sample to be analyzed, and the cartridge has entrance and exit openings 28, 30 to enable the flow through of fluids. One of the stators 16 serves as a fluid injector having numerous ports 32 through which processing fluids can be injected into the cartridge. The other stator 18 serves as a receiver having numerous ports 34 for receiving fluid from the cartridge. Of course, it is possible to utilize some ports in each stator to inject and some ports to receive fluids.

The sample processor 10 can be utilized by loading cartridges 22 into each of the numerous holes 20 of the rotor, with each cartridge being loaded at a loading station 36 and the rotor being turned to bring a new hole to the loading station. Initially, cartridges without samples can be utilized to fill all of the holes of the rotor, and then cartridges containing samples to be analyzed can begin to be loaded while blank cartridges are ejected through an ejector opening 40 formed in one of the stators 16. The rotor is then indexed at predetermined intervals such as every minute, so that, for example, a rotor having twenty two holes 20 uniformly spaced about the rotational axis may be advanced by one-twenty second of a full circle, or about 16.4 degrees, every minute.

As the rotor is indexed, or advanced, each cartridge 22 is brought to one of twenty two stations $S_1$–$S_{22}$ defined about the rotors 16, 18, in a closed path that eventually brings the rotor holes to the initial position. At each station, the cartridge 22 is aligned with a pair of ports 32, 34 in the two stators, so that a particular fluid can flow through the cartridge at that station. The injector stator 16 is provided with couplings 42, each located at a different one of most of the stations, to connect the port 32 in the stator to a pressured supply of a particular fluid that is to be injected into the cartridge. Various types of fluids can be utilized, such as pressured nitrogen for purging, various reagents, and various solvents, depending on the particular processing protocol to be followed. In a similar manner, a group of receiving fittings 44 are connected to the receiving stator 18 to carry away fluid which has flowed through the cartridge. The fluid which is carried away, can lead to various dumping mechanisms such as scrubbers that can hold liquids and absorb gases that should not be released into the atmosphere. One of the receiver fittings 44 will normally be connected to a sensor such as a mass spectrometer, which will be utilized to sense components of the samples to be analyzed.

One of the problems encountered in the processing of chemical samples, arises from the need to contain various gaseous and liquid chemicals, some of which may be applied under pressure and some of which may be harmful if freely released into the atmosphere. Where the sample is retained in the cartridge through much of the processing, good sealing must be obtained between the cartridge openings and the ejector ports, in an automatic and simple manner.

Figure 2:
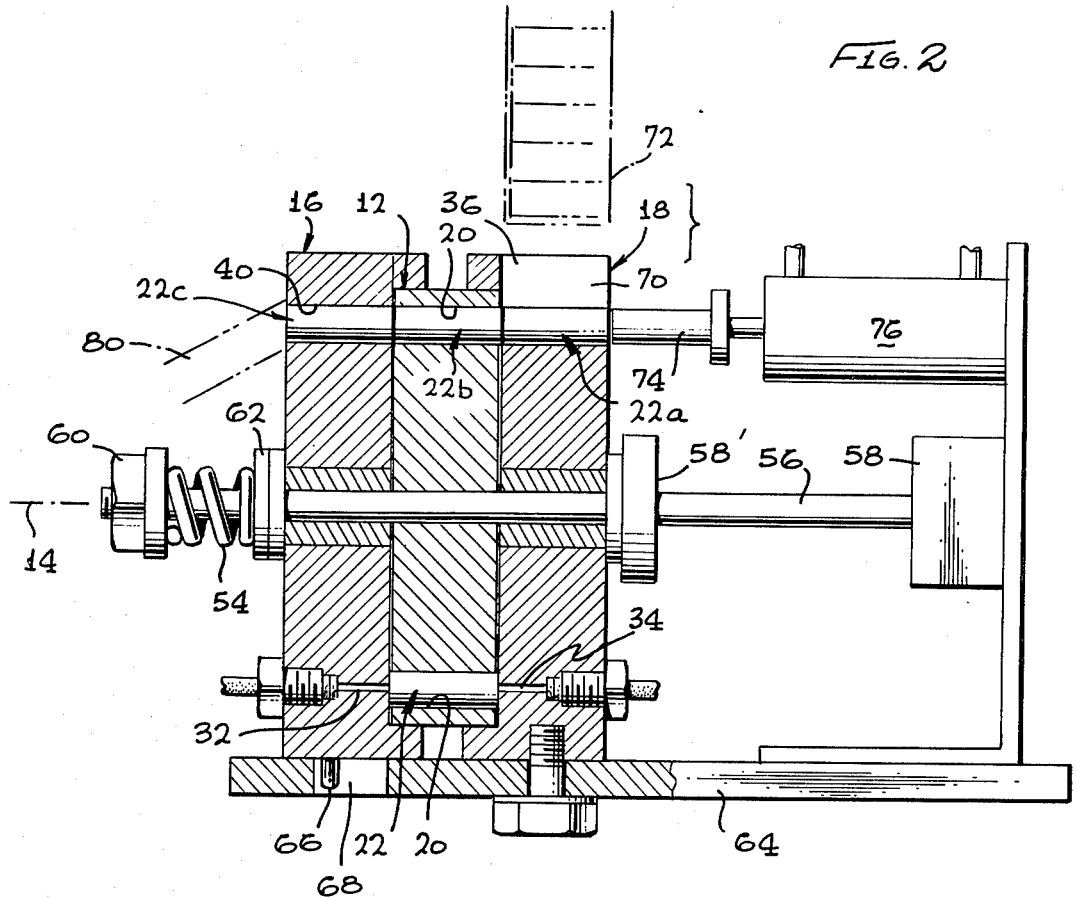
FIG. 2 is a view taken on the line 2—2 of FIG. 1.
Figure 4:
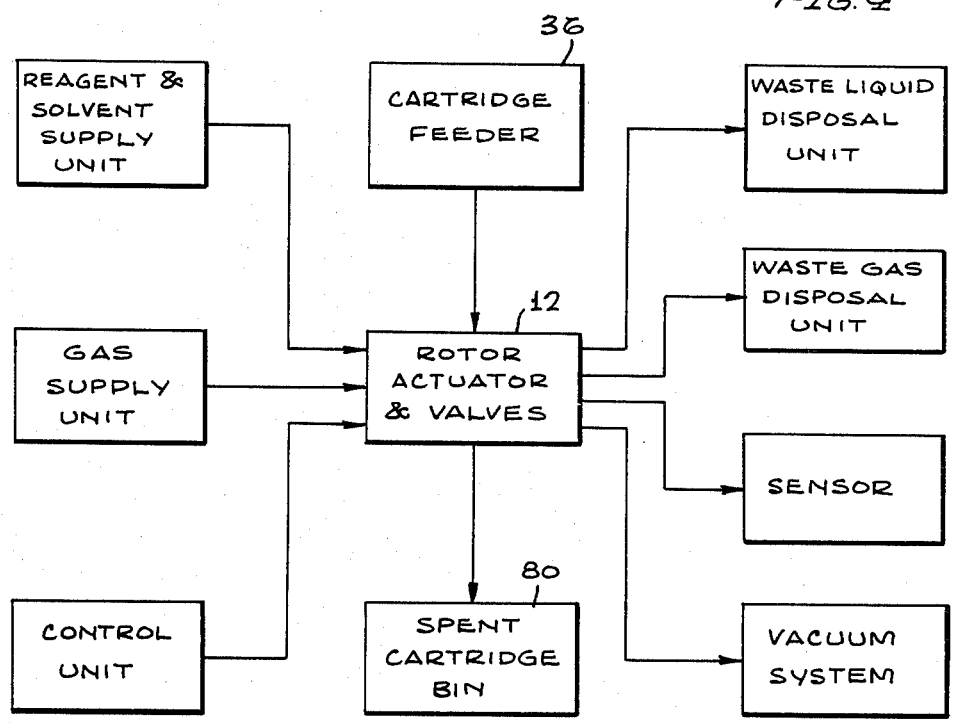
FIG. 4 is a block diagram of a processor system which includes the processor of FIG. 1.

To provide good sealing between the cartridge ends and the stator ports, the cartridge 22 is formed with a length L slightly greater than the thickness of the rotor 12. This causes the extreme ends of the cartridge to project slightly from opposite faces of the rotor. In addition, the stators 16, 18 are provided with flat faces 50, 52 that can form good seals against the ends of the cartridges. In order to assure sealing contact between the cartridge ends and the two stators, one of the stators 16 is mounted, as shown in FIG. 2, so it can move slightly towards and away from the rotor 12, and is biased by a spring 54 towards the other rotor 18.

The rotor 16 is fixed to a shaft 56 that is rotated by an actuating mechanism 58. The actuating mechanism 58 can be formed by a simple geared motor that drives a geneva indexing mechanism, where a simple mechanical stepping mechanism is utilized, or can include a stepping motor driven by a micro processor circuit, where versatile control is required. A collar 58' is fixed to the shaft to bear against the receiver or front stator 18. The spring 54 is captured by a nut 60 at the end of the shaft and bears against a washer 62 to press the rear stator against the rotor. While the front stator 18 can be mounted on a mounting plate 64, the rear stator 16 is slidably along the shaft 56, but is prevented from rotating by a key 66 which extends from the rotor and is received in an axial slot 68 formed in the mounting plate. Thus, the stator faces press against the ends of the cartridge housing, to form a fluid seal thereagainst.

As mentioned above, the numerous holes in the rotor 12 are initially filled with cartridges which may be empty of any sample, and thereafter new cartridges are inserted while processed cartridges are ejected from the rotor. The cartridge changing station 36 includes a cartridge holder in the form of a slot 70 formed in the front stator 18, which can receive one cartridge at a time from a cartridge feeder 72. A plunger 74 operated by a linear actuator 76, can be extended to press one of the cartridges 22a lying in the slot 70 into one of the rotor holes 20 aligned therewith, to insert the cartridge 22a into the corresponding rotor hole. A previous cartridge 22b lying in the rotor hole is then ejected therefrom into a hole 40 formed in the rear stator 16. The previous cartridge 22c lying in the rear stator hole 40 is ejected into a spent cartridge bin 80. Where various valves for controlling the flow of processing fluids are pneumatically operated, the linear actuator 76 can be of the pneumatic cylinder type.

Figure 3:
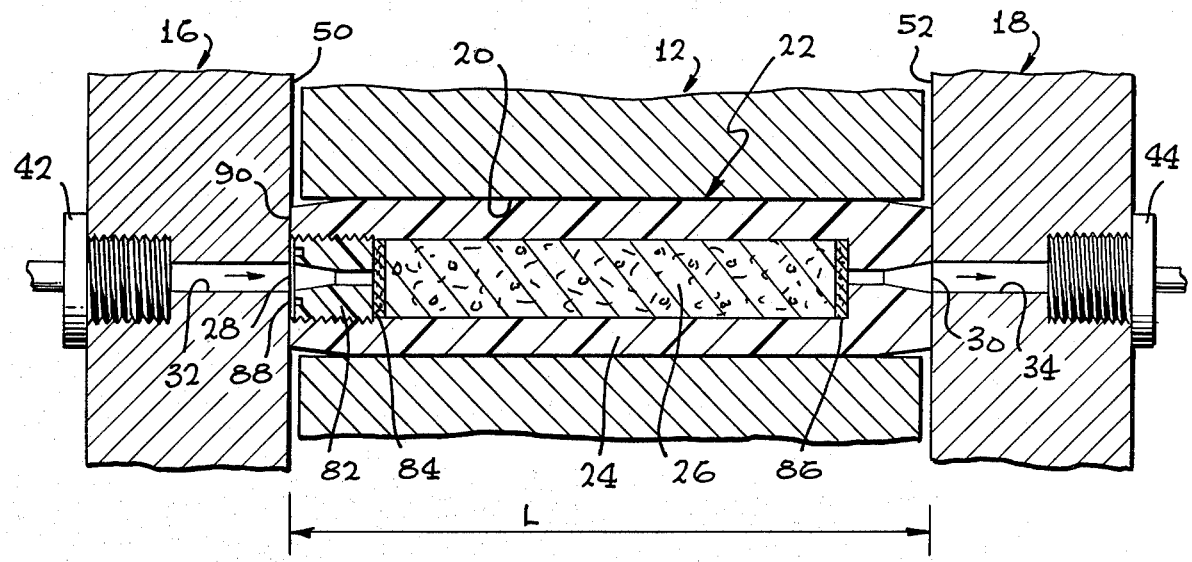
FIG. 3 is an enlarged sectional view of a cartridge utilized in the processor of FIG. 3, showing it held therein.

Each of the cartridges 22 can be formed, as shown in FIG. 3, with a removable plug 82 that facilitates the installation of the packing material 26 and of a pair of filters 84, 86 that permit the passage of fluids while keeping in packing material. A pair of small holes 88 in the plug, permit the insertion of a pronged tool to screw the plug in and out. The plug 82 is normally screwed slightly deeper than the surrounding housing surface 90, so the surface 90 can serve to seal against the stator wall 50. The cartridge housing 24 is formed of an inert and low sliding resistance plastic material such as Teflon. Each of the cartridges can be loaded with a sample off line, that is, prior to insertion of the cartridge into the sample processor 10, although it is possible to utilize one of the injector ports to apply the sample to the cartridge.

Figure 5:
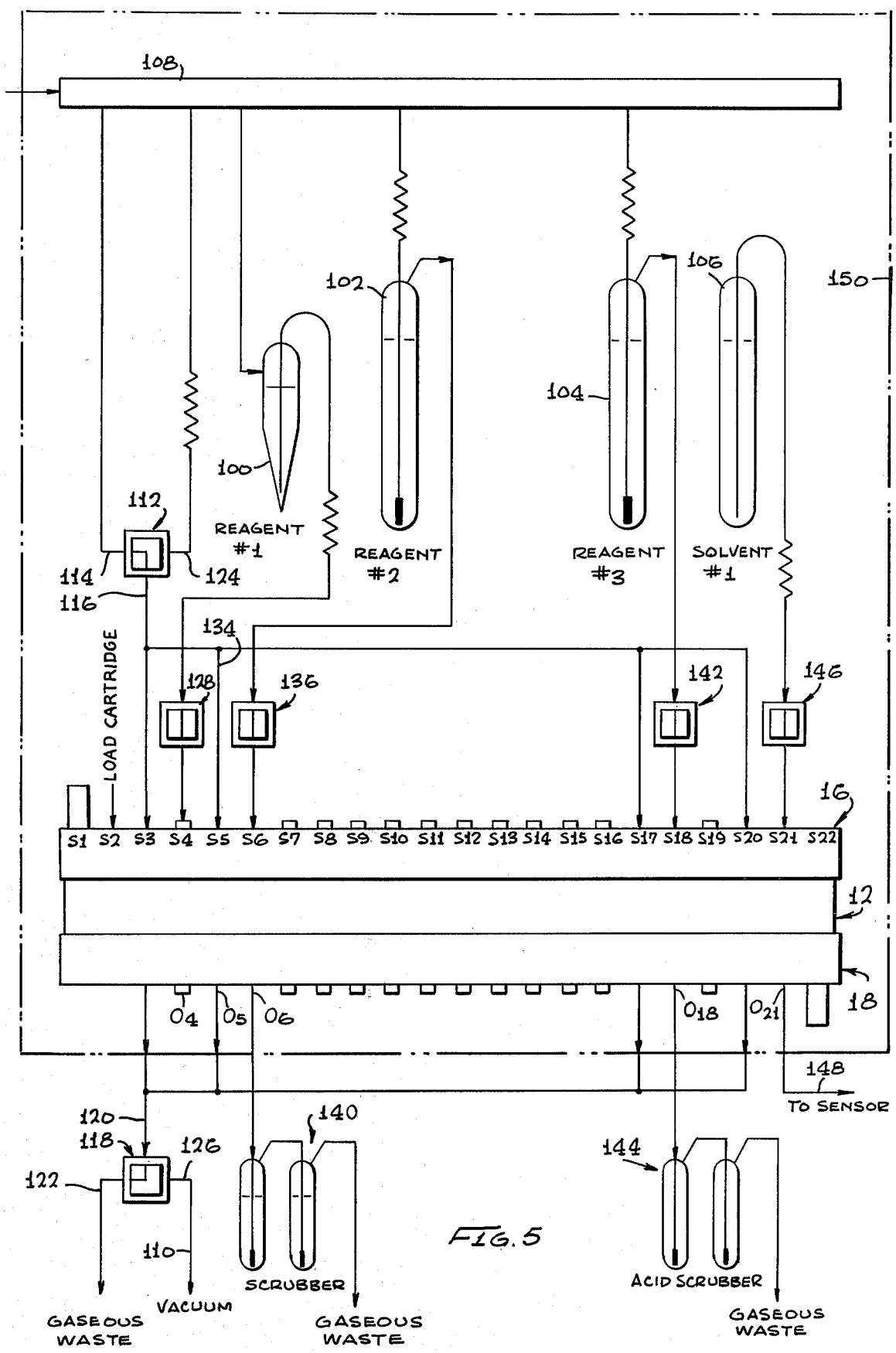
FIG. 5 is a schematic diagram of the processor of FIG. 1.

A better understanding of the operation of the sample processor can be obtained by considering its utilization to perform an automated "free amino acid" protocol using concentrates of amino acids and closely related compounds derived from physiological samples by established ion exchange techniques. FIG. 5 illustrates a system which includes the rotor 12 and stators 16, 18, wherein the stators have been connected to various fluid sources and receivers. Prior to the start of operation of the system, a reservoir 100 is charged with reagent No. 1 which consists of Phenylisothiocyanate in heptane, a second reservoir 102 is charted with reagent No. 2 which consists of an aqueous solution of trimethylamine, a reservoir 104 is charged with reagent No. 3 which consists of trifluoro acetic acid, and a reservoir 106 is charged with a solvent No. 1 which consists of benzene. A source of dry nitrogen at approximately 25 psi is connected to a nitrogen manifold 108, instrument air at approximately 50 psi is connected to an air manifold (not shown) which operates various valves and the cartridge-changing actuator, and a vacuum source at less than one tor is connected to a vacuum line 110. The twenty-two holes of rotor 12 are initially filled with blank cartridges, which have no sample and may not even contain packing material. The cartridge feeder 72 (FIG. 2) is then loaded with cartridges containing standard samples of a known composition, so that data obtained from these cartridges can be utilized for checkout and calibration of the system. Finally, the actuating mechanism 58 is set for the proper timing sequences, as by setting cams of a mechanical timer or appropriately programming a micro processor.

New or recycled sample cartridges are prepared by first thoroughly cleaning them to remove all traces of external contamination and/or residues from previous samples. Meanwhile, the amino acid concentrates are prepared, by adding to the sample a suitable amount of an internal standard solution containing isotropically labelled (e.g., $H^2$, $C^{13}$, $N^{15}$, etc.) equivalents of the amino acids of interest in concentrations similar to the normally expected amounts. Then, amino acid type compounds from physiological samples are isolated from interferring compounds (e.g., peptides) and concentrated by means of ion exchange chromatography using batteries of miniature ion exchange columns in a semi-automatic batch processing mode. Samples from other sources (e.g., peptide sequencers) are used directly after addition of the appropriate internal standard. Next, an aliquot (approximately 25-50 $\mu$-liter) of each amino acid concentrate is injected into the sample cavity of a properly identified cartridge, onto the packing material thereof. Cartridges of different capacity may be utilized for different samples. Finally, the cartridges are loaded in proper sequence into the cartridge feeder. At suitable intervals, blank and standard cartridges (containing a known composition) are inserted between sample cartridges to check on the performance of the system.

The rotor 12 is advanced to bring each cartridge to a next one of the stations $S_1$-$S_{22}$ at predetermined intervals such as once every 60 seconds. A new cartridge is loaded into the rotor at station $S_2$. When the rotor next rotates, the cartridge advances to the station $S_3$. A valve 112 is then switched to connect a first valve inlet 114 to the valve outlet 116, to carry pressured nitrogen from the manifold 108 through the valve to the cartridge, to supply purge gas thereto. At the same time, another valve 118 is operated to connect its inlet 120 to one of its outlets 122 that is coupled to a gaseous waste dump or receiver. After a predetermined purging time such as 20 seconds, the valves 112 and 118 are switched, so that valve 112 then connects its outlet 116 to an inlet 124 that is coupled through a restrictor 126 to the nitrogen manifold 108, to provide a low volume flow of nitrogen, while the valve 118 is switched to connect its outlet 126 to the vacuum line 110.

At then end of the one minute period, the rotor 12 advances to bring the cartridge to the station $S_4$. At that time, a valve 128 is opened for a period such as ten seconds, to permit reagent No. 1 to flow from reservoir 100 through a restrictor 130 into the cartridge, utilizing pressure in the nitrogen manifold to pump out the liquid reagent and apply it under pressure to the cartridge. The outlet port $O_4$ of the front stator 18 is closed off to prevent the outflow of the reagent, and in fact a plug can be used to seal the entire outlet port $O_4$. After ten seconds, the valve 128 closes and the cartridge merely remains at the fourth station for the remainder of the minute. Then, the rotor advances the cartridge to the fifth station $S_5$, wherein the inlet opening of the cartridge is coupled to a fluid line 134 leading to the valve 112 and the outlet opening of the cartridge is coupled through an outlet port $O_5$ that leads to the valve 118. During the one minute period at station $S_5$, the cartridge is again heavily purged with nitrogen for about 20 seconds, and then nitrogen flows at a low rate therethrough, to remove the reagent.

When the cartridge moves to station $S_6$, a valve 136 is opened to carry reagent No. 2 from the reservoir 102 into the cartridge, to saturate the cartridge with the second reagent. It may be noted that the sixth station outlet $O_6$ is coupled through a scrubber 140 to trap potentially polluting chemicals. The scrubber outlet is connected to a gaseous waste dump, which may be a water bath followed by an outlet leading to the atmosphere. During the following ten minutes while the cartridge advances between stations $S_7$ and $S_{16}$, no fluid is added or removed from the cartridge, but time is provided for the second reagent to react on the sample.

At station $S_{17}$, the sample is again subjected to a nitrogen purge to remove excess amounts of the second reagent and volatile reagent by-products, the cartridge then being subjected to a large flow of purging nitrogen followed by a restricted flow. When the cartridge reaches station $S_{18}$, a valve 142 is opened to flow reagent No. 3 from the reservoir 104 through the cartridge to saturate it with the third reagent. The outlet $O_{18}$ is connected to an acid scrubber 144 which leads to the gaseous waste dump, to remove potentially polluting material. The valve 142 may remain open for the entire one minute period, to saturate the sample with the third reagent. During the following minute when the cartridge is at station $S_{19}$, there is no flow into or out of the cartridge, and time is provided for the third reagent to act on the sample. At station $S_{20}$, the cartridge is again subjected to a nitrogen purge.

When the cartridge reaches the station $S_{21}$, a valve 146 is opened, to permit the flow of solvent No. 1 from the reservoir 106 to the cartridge. The solvent flows through the cartridge and through an outlet $O_{21}$ that leads to a fluid line 148. The fluid line 148 leads to a sensor such as a spectrometric or photometric type, to transfer the reaction products of the solvent No. 1 with the remainder of the sample in the cartridge, to the sensor which is continuously operating. The cartridge is then advanced past stations $S_{22}$, the following station $S_1$, and back to the initial station $S_2$. The station $S_2$ is the cartridge replacement station, where a new cartridge is inserted into the rotor and the previous cartridge is ejected.

When the supply of cartridges containing samples to be analyzed, including samples of unknown composition and those of know composition for checking and calibration, have all been installed on the rotor, blank cartridges are utilized to replace the processed cartridges. When a new protocol must be utilized involving the application of different reagents and solvents, appropriate reservoirs are connected to the stators. Small amounts of processing fluids remaining from a previous protocol, can be removed by passing a number of blank cartridges through the system. The same mass spectrometer may be utilized for a wide variety of sample substances. The system can be contained in an enclosure 150 whose atmosphere is closely temperature-controlled, and which can contain an inert gas. The compactness of the processor 10, facilitates the use of such an enclosure.

Thus, the invention provides a sample processor which enables the processing of a batch of samples, utilizing protocols that require the application of pressured gases and various chemicals that must be confined, utilizing a relatively simple and compact apparatus that can be operated to provide a through put of many samples in a relatively short time utilizing a minimum of operator involvement. This can be accomplished by utilizing cartridges loaded with an inert or suitably selective adsorbant packing to hold a sample, and which have ports for admitting and expelling processing fluids. A carriage holds such cartridges to bring them progressively to a number of stations wherein injector and receiving ports are located to enable the passage of various processing fluids, including purging, reagent, and solvent fluids, to the sample. The carriage can comprise a rotor which can rotate between a pair of stators, and with the cartridges having a greater length than the rotor thickness so they seal directly against the walls of the stators. One of the stators can be spring biased towards the other stator, so that the cartridges are pressed in a fluid seal contact against the stators. Any number of cartridges containing samples to be analyzed by the same protocol, can be loaded into sequential holes of the rotor, so that each cartridge is processed in sequence, with each of many cartridges undergoing different steps of the protocol simultaneously, and with the samples (possibly contained in a solvent) of the cartridges drawn off in sequence from the processor to enter a sensor in sequence. Many biological samples are relatively polar, and must be transformed into a volatile derivative and vaporized prior to analysis by gas chromatography. The sealing of the cartridges between stations facilitates such processing, by sealing in vapors, and by isolating reagents utilized at one station, from the other stations.

Although particular embodiments of the invention have been described and illustrated herein, it is recognized that modifications and variations may readily occur to those skilled in the art and consequently, it is intended that the claims be interpreted to cover such modifications and equivalents.

The embodiments of the invention in which an exclusive property or privilege is claimed are defined as follows:

1. A sample processor for chemically processing a sample comprising:
   a sample-holding cartridge having first and second openings and holding a sample material to be processed;
   a carriage constructed to hold said cartridge, said carriage movable to advance a cartridge thereon past a plurality of predetermined stations;
   a plurality of fluid injectors, each having an injector port positioned at a different one of said stations in alignment with a first of said cartridge openings when the cartridge is at said station, said injector constructed to inject a fluid to reach the sample in said cartridge;
   a plurality of fluid receivers, each having a port positioned at a different one of said stations in alignment with a second of said cartridge openings when the cartridge is at said station; and
   a plurality of reagent containers, each containing a fluid reagent which chemically reacts with said sample, each container connected to a selected one of said fluid injectors;
   each of said fluid injectors constructed to apply said fluid to flow it through said cartridge, and said ports forming substantially fluid tight seals with said cartridge around said openings therein.

2. The processor described in claim 1 wherein:
   said carriage has opposite faces and has a hole extending therethrough;
   said cartridge has a length greater than the distance between opposite faces of said carriage, so that opposite ends of the cartridge protrude from said carriage faces and including
   a pair of stators located beyond opposite faces of said carriage and spaced apart by the length of said cartridge to form a fluid seal against said cartridge ends, each of said stators having ports therein facing said carriage with a port in one stator forming said fluid injector port and a port in the other stator forming said fluid receiver.

3. The processor described in claim 2 wherein:
   a first of said stators is movable toward and away from the other stator and is biased thereto.

4. The processor described in claim 1 wherein:
   said cartridge includes an inert housing with open opposite ends and a filler of packing material trapped within the housing to hold a sample.

5. A sample processor comprising:
   a sample-holding cartridge having first and second openings;
   a pair of stators forming a plurality of stations;
   a rotor rotatably mounted between said stators and having a series of cartridge-holding holes therethrough which are evenly spaced thereabout, to bring each cartridge past said stations as the rotor rotates;
   a plurality of fluid injectors, each having an injector port positioned at a different one of said stations in alignment with a first of said cartridge openings when the cartridge is at said station, said injector constructed to inject a fluid to reach the sample in said cartridge;
   a plurality of fluid receivers, each having a port positioned at a different one of said stations in alignment with a second of said cartridge openings when the cartridge is at said station;
   each of said fluid injectors constructed to apply said fluid to flow it through said cartridge, and said ports forming substantially fluid tight seals with said cartridge around said openings therein; and
   loading means positioned along one of said stators, including a cartridge holder positioned to hold a cartridge in line with a hole in said rotor at a predetermined station, and an actuator operable to press a new cartridge lying in the cartridge holder into the rotor hole, so the new cartridge ejects on old one.

6. A sample processor for processing samples container in cartridges, comprising:
   a plurality of sample-holding cartridges that each have opposite ends and an opening at each end;
   a pair of stators having ports;
   a rotor disposed between said stators, and having holes for holding said sample-containing cartridges;
   means for turning said rotor intermittently, to advance each cartridge so the openings therein are aligned with a different pair of ports on said stators; and
   means for applying fluid through selected ports of one stator and receiving fluids from corresponding ports of the other stator, to flow the fluid through the cartridge;
   each of said cartridges having a length greater than the thickness of said rotor, and each including a housing of inert low sliding friction material with ends forming said openings; and
   said stators having substantially flat faces along the paths of said cartridges, and being held together to form fluid tight seals against the cartridge ends.

7. A method for chemically processing samples for analysis, comprising:
   applying said samples to the inside of at least some of a plurality of cartridges;
   mounting said cartridges on a carriage;
   advancing said carriage to advance all of the cartridges thereon at the same time, and to advance each cartridge in sequence past a plurality of stations;
   applying reagent fluids to cartridges lying at selected ones of said stations wherein the reagent fluids are chosen which react with the samples in the cartridges;

each of said cartridges having a pair of openings at opposite ends thereof, and said step of applying fluids includes sealing the walls of an injector port and of a receiving port respectively to said cartridge ends around said openings, flowing said fluid through the injector port into the cartridge and flowing at least some of the fluid out of the cartridge and into the receiving port;

said step of applying including flowing a predetermined reagent through an injector port into the cartridge lying at a first predetermined station, and flowing another fluid through an injector port into the cartridge lying at a second station that is positioned so there is at least one intermediate station between said first and second station; and maintaining a cartridge at said intermediate station substantially without applying or removing fluid therefrom, whereby to provide time for the reagent to react with the sample in one cartridge without hindering the processing of other cartridges travelling along the same path and advanced in unison.

* * * * *